United States Patent
Kunis et al.

(10) Patent No.: US 8,273,084 B2
(45) Date of Patent: *Sep. 25, 2012

(54) ATRIAL ABLATION CATHETER AND METHOD OF USE

(75) Inventors: Christopher G. Kunis, Carlsbad, CA (US); Thomas M. Castellano, Carlsbad, CA (US); Marshall L. Sherman, Carlsbad, CA (US); Randell L. Werneth, Carlsbad, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 585 days.

This patent is subject to a terminal disclaimer.

(21) Appl. No.: 12/197,425

(22) Filed: Aug. 25, 2008

(65) Prior Publication Data

US 2008/0306477 A1    Dec. 11, 2008

Related U.S. Application Data

(63) Continuation of application No. 10/997,172, filed on Nov. 24, 2004, now Pat. No. 7,429,261.

(51) Int. Cl.
*A61B 18/18* (2006.01)
(52) U.S. Cl. .................. 606/41; 606/45; 606/47
(58) Field of Classification Search .......... 606/41, 606/47–50, 116, 122; 607/101, 102
See application file for complete search history.

(56) References Cited

U.S. PATENT DOCUMENTS

| | | |
|---|---|---|
| 3,516,412 A | 6/1970 | Ackerman |
| 3,951,136 A | 4/1976 | Wall |
| 4,017,903 A | 4/1977 | Chu |
| 4,112,952 A | 9/1978 | Thomas et al. |
| 4,411,266 A | 10/1983 | Cosman |
| 4,432,377 A | 2/1984 | Dickhudt |
| 4,660,571 A | 4/1987 | Hess et al. |
| 4,699,147 A | 10/1987 | Chilson et al. |
| 4,785,815 A | 11/1988 | Cohen |
| 4,860,769 A | 8/1989 | Fogarty et al. |
| 4,869,248 A | 9/1989 | Narula |
| 4,882,777 A | 11/1989 | Narula |
| 4,896,671 A | 1/1990 | Cunningham et al. |
| 4,907,589 A | 3/1990 | Cosman |
| 4,920,980 A | 5/1990 | Jackowski |
| 4,940,064 A | 7/1990 | Desai |
| 4,966,597 A | 10/1990 | Cosman |

(Continued)

FOREIGN PATENT DOCUMENTS

AU    5200671    10/2005

(Continued)

OTHER PUBLICATIONS

Oral et al.; U.S. Appl. No. 11/932,378 entitled "Ablation catheters and methods for their use," filed Oct. 31, 2007.

(Continued)

*Primary Examiner* — Linda Dvorak
*Assistant Examiner* — Amanda Scott
(74) *Attorney, Agent, or Firm* — Christopher & Weisberg, P.A.

(57) ABSTRACT

An atrial ablation catheter and methods for its use. The endocardial catheter includes an electrode array particularly adapted to locate and ablate foci of arrhythmia which are required for sustained atrial fibrillation is provided. The array is easily deployed and retracted from the catheter, and presents a distally oriented electrode array that can be pressed against the wall of the atrium.

17 Claims, 6 Drawing Sheets

U.S. PATENT DOCUMENTS

| | | | |
|---|---|---|---|
| 5,010,894 A | 4/1991 | Edhag | |
| 5,016,808 A | 5/1991 | Heil, Jr. et al. | |
| 5,083,565 A | 1/1992 | Parins | |
| 5,100,423 A | 3/1992 | Fearnot | |
| 5,156,151 A | 10/1992 | Imran | |
| 5,184,621 A * | 2/1993 | Vogel et al. | 600/381 |
| 5,215,103 A | 6/1993 | Desai | |
| 5,228,442 A | 7/1993 | Imran | |
| 5,230,349 A | 7/1993 | Langberg | |
| 5,231,987 A | 8/1993 | Robson | |
| 5,231,995 A | 8/1993 | Desai | |
| 5,234,004 A | 8/1993 | Hascoet et al. | |
| 5,239,999 A | 8/1993 | Imran | |
| 5,255,679 A | 10/1993 | Imran | |
| 5,279,299 A | 1/1994 | Imran | |
| 5,281,213 A | 1/1994 | Milder et al. | |
| 5,281,218 A | 1/1994 | Imran | |
| 5,309,910 A | 5/1994 | Edwards et al. | |
| 5,313,943 A | 5/1994 | Houser et al. | |
| 5,318,525 A | 6/1994 | West et al. | |
| 5,324,284 A | 6/1994 | Imran | |
| 5,327,889 A | 7/1994 | Imran | |
| 5,330,466 A | 7/1994 | Imran | |
| 5,334,193 A | 8/1994 | Nardella | |
| 5,342,295 A | 8/1994 | Imran | |
| 5,342,357 A | 8/1994 | Nardella | |
| 5,345,936 A | 9/1994 | Pomeranz et al. | |
| 5,348,554 A | 9/1994 | Imran et al. | |
| D351,652 S | 10/1994 | Thompson et al. | |
| 5,364,352 A | 11/1994 | Cimino et al. | |
| 5,365,926 A | 11/1994 | Desai | |
| 5,370,644 A | 12/1994 | Langberg | |
| 5,383,917 A | 1/1995 | Desai et al. | |
| 5,391,147 A | 2/1995 | Imran et al. | |
| 5,397,304 A | 3/1995 | Truckai | |
| 5,397,339 A | 3/1995 | Desai | |
| 5,400,783 A | 3/1995 | Pomeranz et al. | |
| 5,404,638 A | 4/1995 | Imran | |
| 5,406,946 A | 4/1995 | Imran | |
| 5,411,025 A | 5/1995 | Webster, Jr. | |
| 5,423,808 A | 6/1995 | Edwards et al. | |
| 5,423,811 A | 6/1995 | Imran et al. | |
| 5,433,198 A | 7/1995 | Desai | |
| 5,433,739 A | 7/1995 | Sluijter et al. | |
| 5,445,148 A | 8/1995 | Jaraczewski et al. | |
| 5,462,521 A | 10/1995 | Brucker et al. | |
| 5,462,545 A | 10/1995 | Wang et al. | |
| 5,465,717 A | 11/1995 | Imran et al. | |
| 5,471,982 A | 12/1995 | Edwards et al. | |
| 5,487,757 A | 1/1996 | Truckai et al. | |
| 5,492,119 A | 2/1996 | Abrams | |
| 5,500,011 A | 3/1996 | Desai | |
| 5,507,802 A | 4/1996 | Imran | |
| 5,509,411 A | 4/1996 | Littmann et al. | |
| 5,527,279 A | 6/1996 | Imran | |
| 5,533,967 A | 7/1996 | Imran | |
| 5,536,267 A | 7/1996 | Edwards et al. | |
| 5,540,681 A | 7/1996 | Strul et al. | |
| 5,545,161 A | 8/1996 | Imran | |
| 5,545,193 A | 8/1996 | Fleischman et al. | |
| 5,545,200 A | 8/1996 | West et al. | |
| 5,558,073 A | 9/1996 | Pomeranz et al. | |
| 5,573,533 A | 11/1996 | Strul | |
| 5,575,766 A | 11/1996 | Swartz et al. | |
| 5,575,810 A | 11/1996 | Swanson et al. | |
| 5,578,007 A | 11/1996 | Imran | |
| 5,582,609 A | 12/1996 | Swanson et al. | |
| 5,584,830 A | 12/1996 | Ladd et al. | |
| 5,588,432 A | 12/1996 | Crowley | |
| 5,588,964 A | 12/1996 | Imran et al. | |
| 5,595,183 A | 1/1997 | Swanson et al. | |
| 5,596,995 A | 1/1997 | Sherman et al. | |
| 5,598,848 A | 2/1997 | Swanson et al. | |
| 5,601,088 A | 2/1997 | Swanson et al. | |
| 5,606,974 A | 3/1997 | Castellano et al. | |
| 5,607,462 A | 3/1997 | Imran | |
| 5,620,481 A | 4/1997 | Desai et al. | |
| 5,626,136 A | 5/1997 | Webster, Jr. | |
| 5,630,425 A | 5/1997 | Panescu et al. | |
| 5,630,837 A | 5/1997 | Crowley | |
| 5,637,090 A | 6/1997 | McGee et al. | |
| D381,076 S | 7/1997 | Thornton et al. | |
| 5,645,064 A | 7/1997 | Littmann et al. | |
| 5,645,082 A | 7/1997 | Sung et al. | |
| 5,656,029 A | 8/1997 | Imran et al. | |
| 5,657,755 A | 8/1997 | Desai | |
| 5,658,278 A | 8/1997 | Imran et al. | |
| 5,662,606 A | 9/1997 | Cimino et al. | |
| 5,666,970 A | 9/1997 | Smith | |
| 5,673,695 A | 10/1997 | McGee et al. | |
| 5,680,860 A | 10/1997 | Imran | |
| 5,681,280 A | 10/1997 | Rusk et al. | |
| 5,682,885 A | 11/1997 | Littmann et al. | |
| 5,685,322 A | 11/1997 | Sung et al. | |
| 5,687,723 A | 11/1997 | Avitall | |
| 5,693,078 A | 12/1997 | Desai et al. | |
| 5,697,927 A | 12/1997 | Imran et al. | |
| 5,697,928 A | 12/1997 | Walcott et al. | |
| 5,699,796 A | 12/1997 | Littmann et al. | |
| 5,702,438 A | 12/1997 | Avitall | |
| 5,704,791 A | 1/1998 | Gillio | |
| 5,706,809 A | 1/1998 | Littmann et al. | |
| 5,711,298 A | 1/1998 | Littmann et al. | |
| 5,716,389 A | 2/1998 | Walinsky et al. | |
| 5,722,401 A | 3/1998 | Pietroski et al. | |
| 5,722,975 A | 3/1998 | Edwards et al. | |
| 5,724,985 A | 3/1998 | Snell et al. | |
| 5,733,323 A | 3/1998 | Buck et al. | |
| 5,735,280 A | 4/1998 | Sherman et al. | |
| 5,741,320 A | 4/1998 | Thornton et al. | |
| 5,766,152 A | 6/1998 | Morley et al. | |
| 5,769,791 A | 6/1998 | Benaron et al. | |
| 5,769,847 A | 6/1998 | Panescu et al. | |
| 5,772,590 A | 6/1998 | Webster, Jr. | |
| 5,775,327 A | 7/1998 | Randolph et al. | |
| 5,782,239 A | 7/1998 | Webster, Jr. | |
| 5,782,760 A | 7/1998 | Schaer | |
| 5,782,828 A | 7/1998 | Chen et al. | |
| 5,782,899 A | 7/1998 | Imran | |
| 5,792,140 A | 8/1998 | Tu et al. | |
| 5,800,482 A | 9/1998 | Pomeranz et al. | |
| 5,810,740 A | 9/1998 | Paisner | |
| 5,820,568 A | 10/1998 | Willis | |
| 5,827,272 A | 10/1998 | Breining et al. | |
| 5,837,001 A | 11/1998 | Mackey | |
| 5,849,028 A | 12/1998 | Chen | |
| 5,857,464 A | 1/1999 | Desai | |
| 5,857,997 A | 1/1999 | Cimino et al. | |
| 5,860,920 A | 1/1999 | McGee et al. | |
| 5,863,291 A | 1/1999 | Schaer | |
| 5,871,523 A | 2/1999 | Fleischman et al. | |
| 5,873,865 A | 2/1999 | Horzewski et al. | |
| 5,876,399 A | 3/1999 | Chia et al. | |
| 5,881,732 A | 3/1999 | Sung et al. | |
| 5,882,333 A | 3/1999 | Schaer et al. | |
| 5,885,278 A | 3/1999 | Fleischman | |
| 5,891,027 A | 4/1999 | Tu et al. | |
| 5,891,135 A | 4/1999 | Jackson et al. | |
| 5,891,137 A | 4/1999 | Chia et al. | |
| 5,891,138 A | 4/1999 | Tu et al. | |
| 5,893,847 A | 4/1999 | Kordis | |
| 5,893,884 A | 4/1999 | Tu | |
| 5,893,885 A | 4/1999 | Webster, Jr. | |
| 5,895,355 A | 4/1999 | Schaer | |
| 5,895,417 A | 4/1999 | Pomeranz et al. | |
| 5,897,554 A | 4/1999 | Chia et al. | |
| 5,904,680 A | 5/1999 | Kordis et al. | |
| 5,906,605 A | 5/1999 | Coxum | |
| 5,910,129 A | 6/1999 | Koblish et al. | |
| 5,911,720 A | 6/1999 | Bourne et al. | |
| 5,913,854 A | 6/1999 | Maguire et al. | |
| 5,916,214 A | 6/1999 | Cosio et al. | |
| 5,928,191 A | 7/1999 | Houser et al. | |
| 5,931,835 A | 8/1999 | Mackey | |
| 5,935,063 A | 8/1999 | Nguyen | |
| 5,938,694 A | 8/1999 | Jaraczewski et al. | |
| 5,941,845 A | 8/1999 | Tu et al. | |

| | | |
|---|---|---|
| 5,951,471 A | 9/1999 | de la Rama et al. |
| 5,954,719 A | 9/1999 | Chen et al. |
| 5,957,842 A | 9/1999 | Littmann et al. |
| 5,960,796 A | 10/1999 | Sung et al. |
| 5,967,978 A | 10/1999 | Littmann et al. |
| 5,968,040 A | 10/1999 | Swanson et al. |
| 5,971,980 A | 10/1999 | Sherman |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,004,269 A | 12/1999 | Crowley et al. |
| 6,014,581 A | 1/2000 | Whayne et al. |
| 6,021,340 A | 2/2000 | Randolph et al. |
| 6,023,638 A | 2/2000 | Swanson |
| 6,029,091 A | 2/2000 | de la Rama et al. |
| 6,032,674 A | 3/2000 | Eggers et al. |
| 6,033,403 A | 3/2000 | Tu et al. |
| 6,042,580 A | 3/2000 | Simpson |
| 6,045,550 A | 4/2000 | Simpson et al. |
| 6,048,329 A | 4/2000 | Thompson et al. |
| 6,049,737 A | 4/2000 | Simpson et al. |
| 6,050,994 A | 4/2000 | Sherman |
| 6,052,612 A | 4/2000 | Desai |
| 6,053,937 A | 4/2000 | Edwards et al. |
| 6,056,744 A | 5/2000 | Edwards |
| 6,059,778 A | 5/2000 | Sherman |
| 6,063,077 A | 5/2000 | Schaer |
| 6,063,082 A | 5/2000 | DeVore et al. |
| 6,064,902 A | 5/2000 | Haissaguerre et al. |
| 6,068,629 A | 5/2000 | Haissaguerre et al. |
| 6,070,094 A | 5/2000 | Swanson et al. |
| 6,071,274 A | 6/2000 | Thompson et al. |
| 6,071,279 A | 6/2000 | Whayne et al. |
| 6,071,281 A | 6/2000 | Burnside et al. |
| 6,071,282 A * | 6/2000 | Fleischman .................. 606/41 |
| 6,074,351 A | 6/2000 | Houser |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson et al. |
| 6,106,522 A | 8/2000 | Fleischman et al. |
| 6,107,699 A | 8/2000 | Swanson |
| 6,115,626 A | 9/2000 | Whayne et al. |
| 6,119,041 A | 9/2000 | Pomeranz et al. |
| 6,120,476 A | 9/2000 | Fung et al. |
| 6,129,724 A | 10/2000 | Fleischman et al. |
| 6,141,576 A | 10/2000 | Littmann et al. |
| 6,146,379 A | 11/2000 | Fleischman et al. |
| 6,146,381 A | 11/2000 | Bowe et al. |
| 6,165,169 A | 12/2000 | Panescu et al. |
| 6,167,291 A | 12/2000 | Barajas et al. |
| 6,171,305 B1 | 1/2001 | Sherman |
| 6,171,306 B1 | 1/2001 | Swanson et al. |
| 6,179,833 B1 | 1/2001 | Taylor |
| 6,200,314 B1 | 3/2001 | Sherman |
| 6,212,426 B1 | 4/2001 | Swanson |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,573 B1 | 4/2001 | Webster |
| 6,217,576 B1 | 4/2001 | Tu et al. |
| 6,226,542 B1 | 5/2001 | Reisfeld |
| 6,231,570 B1 | 5/2001 | Tu et al. |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,725 B1 | 6/2001 | Cosman |
| 6,241,726 B1 | 6/2001 | Raymond Chia et al. |
| 6,241,727 B1 | 6/2001 | Tu et al. |
| 6,241,728 B1 | 6/2001 | Gaiser et al. |
| 6,241,754 B1 | 6/2001 | Swanson et al. |
| 6,245,067 B1 | 6/2001 | Tu et al. |
| 6,245,089 B1 | 6/2001 | Daniel et al. |
| 6,251,107 B1 | 6/2001 | Schaer |
| 6,256,540 B1 | 7/2001 | Panescu et al. |
| 6,264,664 B1 | 7/2001 | Avellanet |
| 6,267,746 B1 | 7/2001 | Bumbalough |
| 6,290,697 B1 | 9/2001 | Tu et al. |
| 6,293,943 B1 | 9/2001 | Panescu et al. |
| 6,302,880 B1 | 10/2001 | Schaer |
| 6,309,385 B1 | 10/2001 | Simpson |
| 6,312,425 B1 | 11/2001 | Simpson et al. |
| 6,319,251 B1 * | 11/2001 | Tu et al. ..................... 606/41 |
| 6,325,797 B1 | 12/2001 | Stewart et al. |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson et al. |
| 6,360,128 B2 | 3/2002 | Kordis et al. |
| 6,370,435 B2 | 4/2002 | Panescu et al. |
| 6,371,955 B1 | 4/2002 | Fuimaono et al. |
| 6,379,352 B1 | 4/2002 | Reynolds et al. |
| 6,389,311 B1 | 5/2002 | Whayne et al. |
| 6,391,024 B1 | 5/2002 | Sun et al. |
| 6,425,894 B1 | 7/2002 | Brucker et al. |
| 6,428,536 B2 | 8/2002 | Panescu et al. |
| 6,428,537 B1 | 8/2002 | Swanson et al. |
| 6,440,129 B1 | 8/2002 | Simpson |
| 6,447,506 B1 | 9/2002 | Swanson et al. |
| 6,451,015 B1 | 9/2002 | Rittman, III et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,693 B1 | 10/2002 | Carroll et al. |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest et al. |
| 6,478,793 B1 | 11/2002 | Cosman et al. |
| 6,485,487 B1 | 11/2002 | Sherman |
| 6,487,441 B1 | 11/2002 | Swanson et al. |
| 6,488,678 B2 | 12/2002 | Sherman |
| 6,490,468 B2 | 12/2002 | Panescu et al. |
| 6,493,586 B1 | 12/2002 | Stahmann et al. |
| 6,500,167 B1 | 12/2002 | Webster, Jr. |
| 6,500,172 B1 | 12/2002 | Panescu et al. |
| 6,514,246 B1 | 2/2003 | Swanson et al. |
| 6,517,536 B2 | 2/2003 | Hooven et al. |
| 6,522,905 B2 | 2/2003 | Desai |
| 6,529,756 B1 | 3/2003 | Phan et al. |
| 6,540,744 B2 | 4/2003 | Hassett et al. |
| 6,542,773 B2 | 4/2003 | Dupree et al. |
| 6,544,262 B2 | 4/2003 | Fleischman |
| 6,551,271 B2 | 4/2003 | Nguyen |
| 6,554,794 B1 | 4/2003 | Mueller et al. |
| 6,558,378 B2 | 5/2003 | Sherman et al. |
| 6,565,511 B2 | 5/2003 | Panescu et al. |
| 6,569,114 B2 | 5/2003 | Ponzi et al. |
| 6,569,162 B2 | 5/2003 | He |
| 6,569,163 B2 | 5/2003 | Hata et al. |
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,583,796 B2 | 6/2003 | Jamar et al. |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,607,520 B2 | 8/2003 | Keane |
| 6,616,657 B2 | 9/2003 | Simpson et al. |
| 6,625,482 B1 | 9/2003 | Panescu et al. |
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,223 B2 | 10/2003 | Lifshitz et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,652,517 B1 | 11/2003 | Hall et al. |
| 6,658,279 B2 | 12/2003 | Swanson et al. |
| 6,669,692 B1 | 12/2003 | Nelson et al. |
| 6,669,693 B2 | 12/2003 | Friedman |
| 6,671,533 B2 | 12/2003 | Chen et al. |
| 6,690,972 B2 | 2/2004 | Conley et al. |
| 6,701,180 B1 | 3/2004 | Desai |
| 6,702,811 B2 | 3/2004 | Stewart et al. |

| | | |
|---|---|---|
| 6,711,428 B2 | 3/2004 | Fuimaono et al. |
| 6,730,078 B2 | 5/2004 | Simpson et al. |
| 6,738,673 B2 | 5/2004 | Desai |
| 6,740,080 B2 | 5/2004 | Jain et al. |
| 6,743,225 B2 | 6/2004 | Sanchez et al. |
| 6,746,446 B1 | 6/2004 | Hill, III et al. |
| 6,752,804 B2 | 6/2004 | Simpson et al. |
| 6,761,716 B2 | 7/2004 | Kadhiresan et al. |
| 6,805,131 B2 | 10/2004 | Kordis |
| 6,813,520 B2 | 11/2004 | Sampson et al. |
| 6,814,732 B2 | 11/2004 | Schaer |
| 6,830,576 B2 | 12/2004 | Fleischman et al. |
| 6,866,662 B2 | 3/2005 | Fuimaono et al. |
| 6,893,438 B2 | 5/2005 | Hall et al. |
| 6,893,439 B2 | 5/2005 | Fleischman |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 * | 10/2005 | Satake ......................... 607/102 |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 12/2005 | Hill, III et al. |
| 6,973,339 B2 | 12/2005 | Govari |
| 6,987,995 B2 | 1/2006 | Drysen |
| 7,001,336 B2 | 2/2006 | Mandrusov et al. |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Fuimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai et al. |
| 7,155,270 B2 | 12/2006 | Solis et al. |
| 7,156,843 B2 | 1/2007 | Skarda |
| 7,163,537 B2 | 1/2007 | Lee et al. |
| 2001/0029366 A1 | 10/2001 | Swanson et al. |
| 2001/0039415 A1 | 11/2001 | Francischelli et al. |
| 2001/0044625 A1 | 11/2001 | Hata et al. |
| 2001/0051803 A1 | 12/2001 | Desai et al. |
| 2002/0065465 A1 | 5/2002 | Panescu et al. |
| 2002/0120263 A1 | 8/2002 | Brown et al. |
| 2002/0126036 A1 | 9/2002 | Flaherty et al. |
| 2002/0161422 A1 | 10/2002 | Swanson et al. |
| 2003/0018330 A1 | 1/2003 | Swanson et al. |
| 2003/0093069 A1 | 5/2003 | Panescu et al. |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman et al. |
| 2003/0199746 A1 | 10/2003 | Fuimaono et al. |
| 2003/0204185 A1 | 10/2003 | Sherman et al. |
| 2003/0204186 A1 | 10/2003 | Geistert |
| 2004/0015164 A1 | 1/2004 | Fuimaono et al. |
| 2004/0082947 A1 | 4/2004 | Oral et al. |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Bednarek |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfery |
| 2004/0236324 A1 | 11/2004 | Muller et al. |
| 2004/0247164 A1 | 12/2004 | Furnish |
| 2005/0010095 A1 | 1/2005 | Stewart et al. |
| 2005/0015084 A1 | 1/2005 | Hill et al. |
| 2005/0033137 A1 | 2/2005 | Oral et al. |
| 2005/0065512 A1 | 3/2005 | Schaer |
| 2005/0096644 A1 | 5/2005 | Hall et al. |
| 2005/0101946 A1 | 5/2005 | Govari et al. |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 | 4/2006 | Werneth et al. |
| 2006/0095030 A1 | 5/2006 | Avitall et al. |
| 2006/0106375 A1 | 5/2006 | Werneth et al. |
| 2006/0111700 A1 | 5/2006 | Kunis et al. |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0142753 A1 | 6/2006 | Francischelli et al. |
| 2006/0189975 A1 | 8/2006 | Whayne et al. |
| 2006/0195082 A1 | 8/2006 | Francischelli |
| 2006/0241366 A1 | 10/2006 | Falwell et al. |
| 2007/0083193 A1 | 4/2007 | Werneth et al. |
| 2007/0083194 A1 | 4/2007 | Kunis et al. |
| 2007/0083195 A1 | 4/2007 | Werneth et al. |
| 2007/0106293 A1 | 5/2007 | Oral et al. |

FOREIGN PATENT DOCUMENTS

| | | |
|---|---|---|
| CA | 2327322 | 11/1999 |
| CA | 2327518 | 11/1999 |
| CA | 2328064 | 11/1999 |
| CA | 2328070 | 11/1999 |
| CA | 2371935 | 12/2000 |
| CA | 2222617 C | 7/2002 |
| CA | 2437140 | 6/2004 |
| CA | 2492283 | 7/2005 |
| CA | 2194061 C | 4/2006 |
| CA | 2276755 C | 5/2006 |
| CA | 2251041 C | 6/2006 |
| EP | 428812 B1 | 3/1995 |
| EP | 779059 A | 6/1997 |
| EP | 598742 B1 | 8/1999 |
| EP | 879016 B1 | 10/2003 |
| EP | 1360938 A1 | 11/2003 |
| EP | 1364677 A2 | 11/2003 |
| EP | 1554986 A1 | 7/2005 |
| EP | 823843 B1 | 10/2005 |
| EP | 13844456 B1 | 2/2006 |
| EP | 1169976 B1 | 4/2006 |
| EP | 1415680 B1 | 4/2006 |
| EP | 1011437 B1 | 5/2006 |
| EP | 1210021 B1 | 5/2006 |
| EP | 1658818 A1 | 5/2006 |
| EP | 1125549 B1 | 6/2006 |
| EP | 1182980 B1 | 6/2006 |
| EP | 1207798 B1 | 6/2006 |
| EP | 1321166 B1 | 7/2006 |
| EP | 1343427 B1 | 7/2006 |
| EP | 828451 B1 | 9/2006 |
| EP | 1070480 B1 | 9/2006 |
| EP | 1014874 B1 | 12/2006 |
| EP | 1383437 B1 | 12/2006 |
| EP | 1455667 B1 | 1/2007 |
| EP | 957794 B1 | 7/2007 |
| JP | 2004188179 A | 7/2004 |
| SU | 1512622 A1 | 10/1989 |
| SU | 1544396 A1 | 2/1990 |
| SU | 1690786 A1 | 11/1991 |
| WO | WO90/06079 A1 | 6/1990 |
| WO | WO93/08756 A1 | 5/1993 |
| WO | WO93/25273 A1 | 12/1993 |
| WO | WO94/12098 A1 | 6/1994 |
| WO | WO96/10961 A1 | 4/1996 |
| WO | WO96/32885 A1 | 10/1996 |

| | | | |
|---|---|---|---|
| WO | WO96/32897 A1 | 10/1996 |
| WO | WO96/34558 A1 | 11/1996 |
| WO | WO96/34559 A1 | 11/1996 |
| WO | WO96/34560 A1 | 11/1996 |
| WO | WO96/34567 A1 | 11/1996 |
| WO | WO96/34569 A1 | 11/1996 |
| WO | WO96/34570 A1 | 11/1996 |
| WO | WO96/34650 A1 | 11/1996 |
| WO | WO96/34652 A1 | 11/1996 |
| WO | WO96/34653 A1 | 11/1996 |
| WO | WO96/36860 A2 | 11/1996 |
| WO | WO96/39967 A1 | 12/1996 |
| WO | WO97/15919 A1 | 5/1997 |
| WO | WO97/17893 A1 | 5/1997 |
| WO | WO97/17904 A1 | 5/1997 |
| WO | WO97/25917 A1 | 7/1997 |
| WO | WO97/25919 A1 | 7/1997 |
| WO | WO97/32525 A1 | 9/1997 |
| WO | WO97/36541 A1 | 10/1997 |
| WO | WO97/40760 A1 | 11/1997 |
| WO | WO97/42996 A1 | 11/1997 |
| WO | WO98/18520 A2 | 5/1998 |
| WO | WO98/19611 A1 | 5/1998 |
| WO | WO98/26724 A1 | 6/1998 |
| WO | WO98/28039 A2 | 7/1998 |
| WO | WO98/38913 A1 | 9/1998 |
| WO | WO99/02096 A1 | 1/1999 |
| WO | WO99/56644 A1 | 11/1999 |
| WO | WO99/56647 A1 | 11/1999 |
| WO | WO99/56648 A1 | 11/1999 |
| WO | WO99/56649 A1 | 11/1999 |
| WO | WO00/78239 A2 | 12/2000 |
| WO | WO02/060523 A2 | 8/2002 |
| WO | WO03/041602 A2 | 5/2003 |
| WO | WO03/089997 A2 | 10/2003 |
| WO | WO2005/027765 A1 | 3/2005 |
| WO | WO2005/027766 A1 | 3/2005 |
| WO | WO2005/065562 A1 | 7/2005 |
| WO | WO2005/065563 A1 | 7/2005 |
| WO | WO2005/104972 A2 | 11/2005 |
| WO | WO2006/017517 A2 | 2/2006 |
| WO | WO2006/044794 A2 | 4/2006 |
| WO | WO2006/049970 A2 | 5/2006 |
| WO | WO2006/052651 A1 | 5/2006 |
| WO | WO2006/052905 A2 | 5/2006 |
| WO | WO2006/055654 A1 | 5/2006 |
| WO | WO2006/055658 A1 | 5/2006 |
| WO | WO2006/055733 A1 | 5/2006 |
| WO | WO2006/055741 A1 | 5/2006 |

OTHER PUBLICATIONS

"Werneth et al.; U.S. Appl. No. 12/116,753 entitled ""Ablation therapy system and method for treating continuous atrial fibrillation,"" filed May 7, 2008".

Sherman et. al. ; U.S. Appl. No. 12/117,596 entitled RF energy delivery system and method, filed May 8, 2008.

Oral et al.; U.S. Appl. No. 12/176,115 entitled "Atrial ablation catheter adapted for treatment of septal wall arrhythmogenic foci and method of use," filed Jul. 18, 2008.

Werneth et al.; U.S. Appl. No. 12/245,625 entitled "Ablation catheter," filed Oct. 3, 2008.

Oral et al., "Catheter ablation for paroxysmal atrial fibrillation: segmental pulmonary vein ostial ablation versus left atrial ablation," Circulation, vol. 108, pp. 2355-2360.

Oral et al., "Segmental ostial ablation to isolate the pulmonary veins during atrial fibrillation: feasibility and mechanistic insights," Circulation, vol. 106, pp. 1256-1262.

Nademanee et al., "A new approach for catheter ablation of atrial fibrillation: mapping of the electrophysiologic substrate," JACC, vol. 43, No. 11, pp. 2044-2053, 2004.

Wittkampf et al., "Radiofrequency ablation with a cooled porous electrode catheter," (abstract) JACC, vol. 11, No. 2, pp. 17a, Feb. 1988.

* cited by examiner

Patch Electrode

Control System

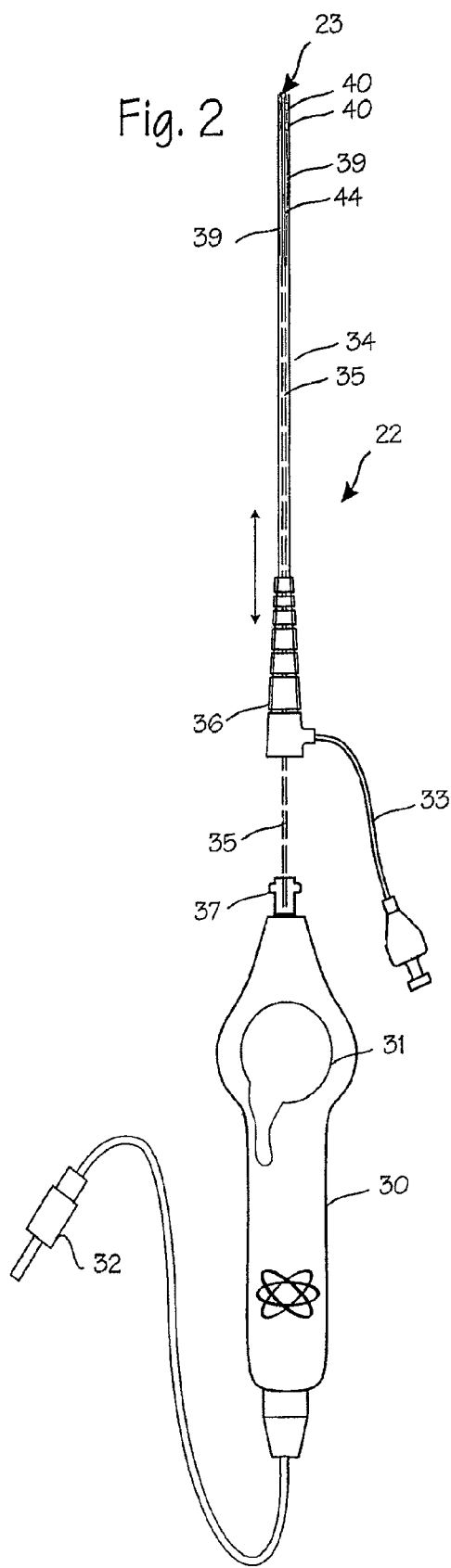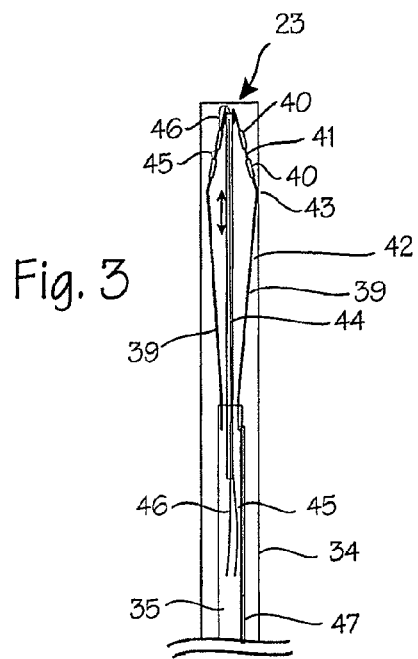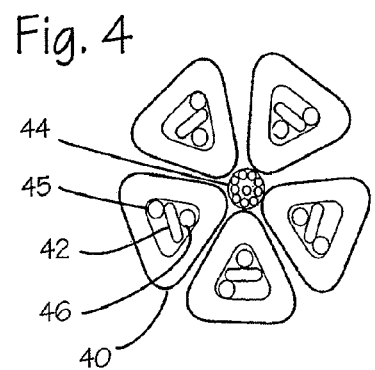

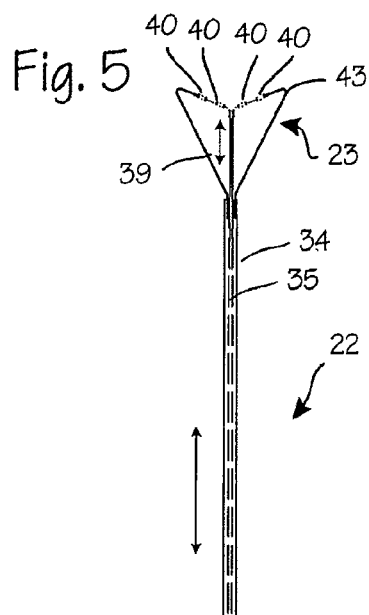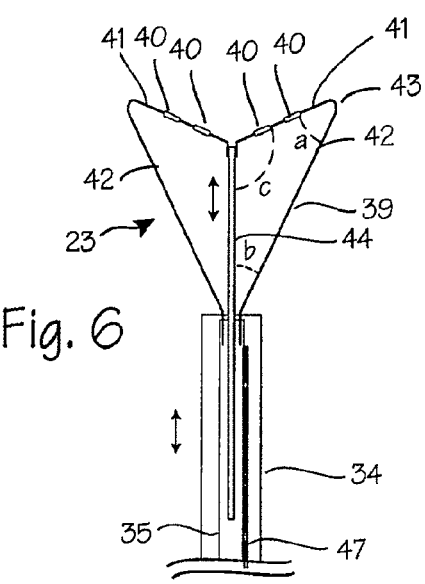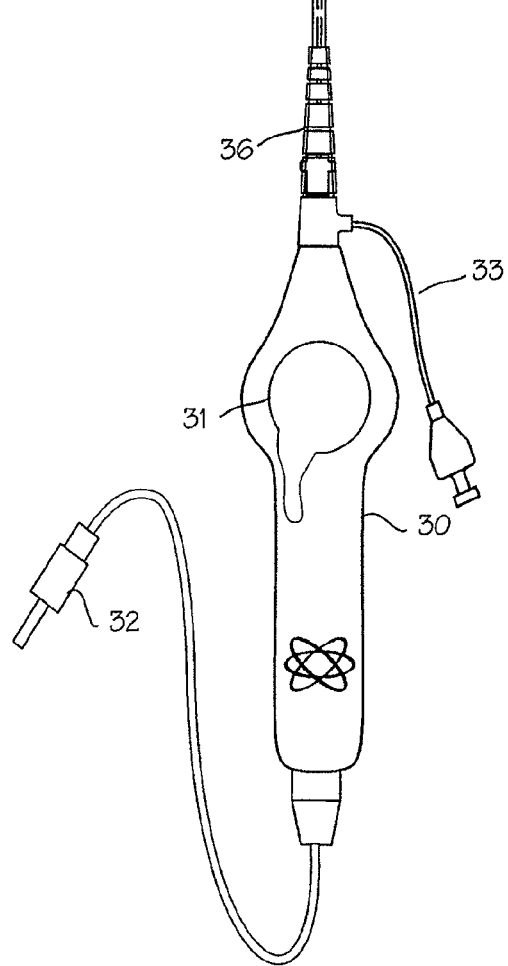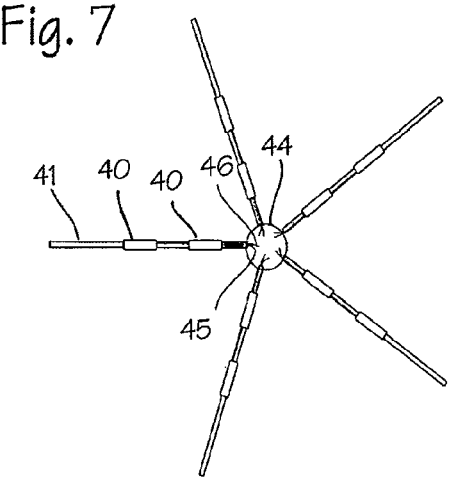

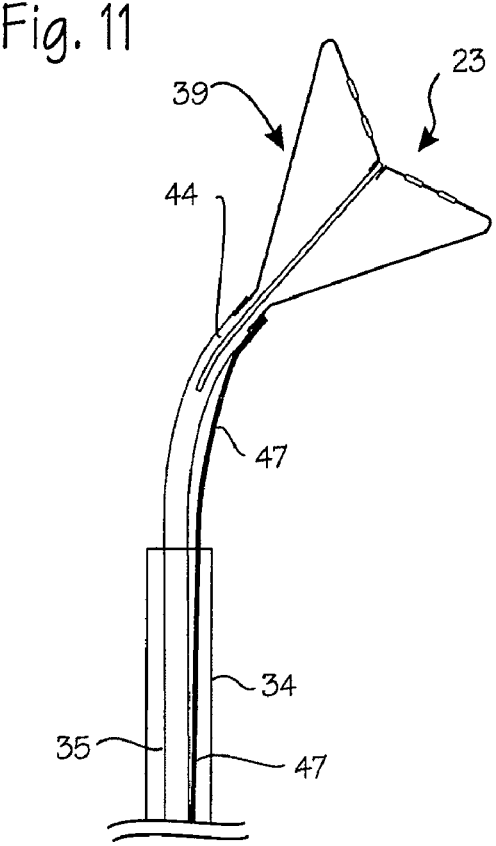
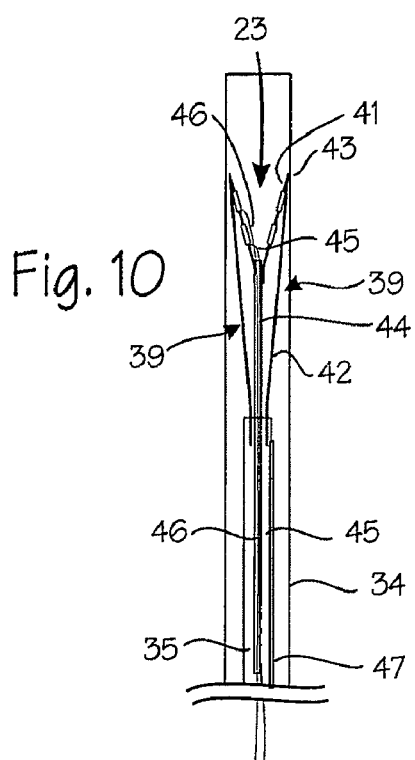
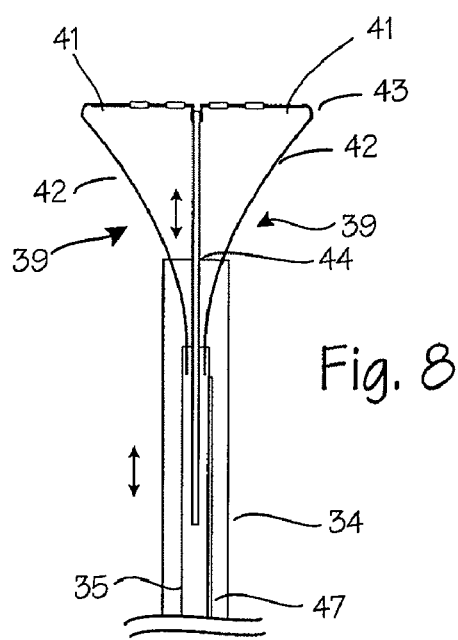
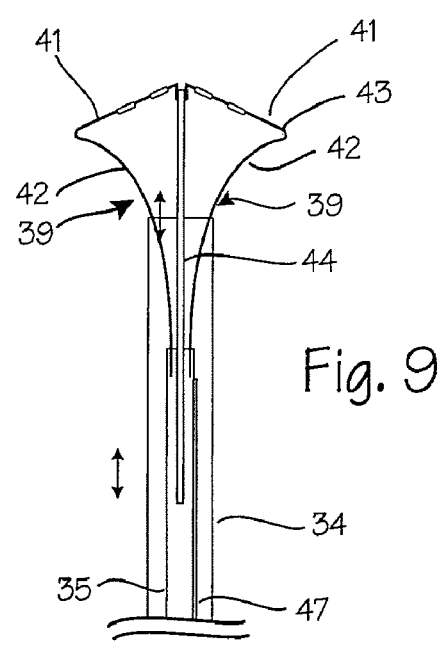

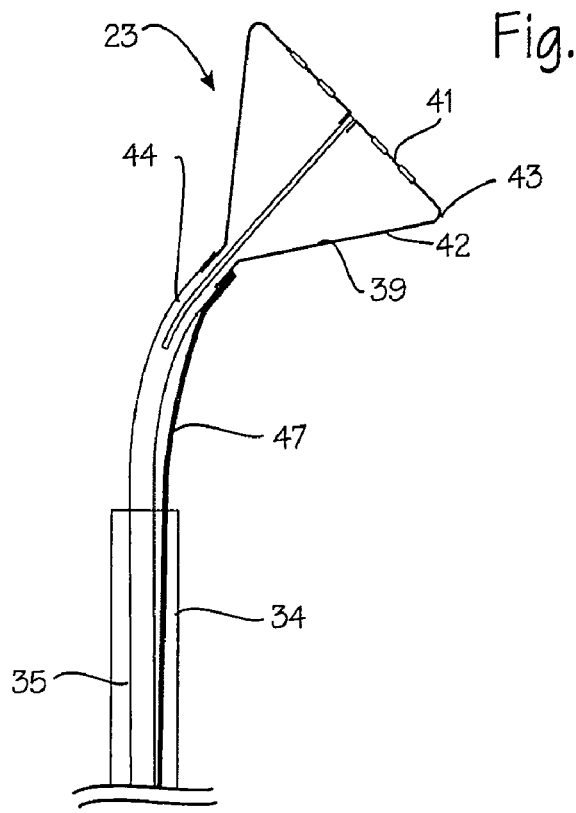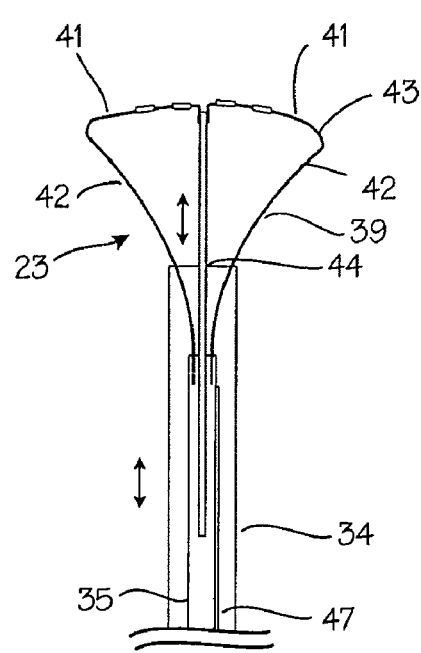

US 8,273,084 B2

ATRIAL ABLATION CATHETER AND METHOD OF USE

CROSS REFERENCE TO RELATED APPLICATIONS

This application is a continuation of U.S. patent application Ser. No. 10/997,172, filed Nov. 24, 2004 entitled "Atrial Ablation Catheter and Method of Use," U.S. Pat. No. 7,429,261.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The inventions described below relate the field of atrial ablation.

BACKGROUND OF THE INVENTION

Atrial fibrillation is a form of arrhythmia, or irregular heartbeat, in which the atria (the two small upper chambers of the heart) quiver instead of beating effectively. While there are a number of variations of atrial fibrillation with different causes, they all involve irregularities in the transmission of electrical impulses through the heart. As a result of abnormalities in the heart's electrical impulses, the heart is not able to pump the blood out properly, and it may pool and clot. If a blood clot moves to an artery in the brain, AF can lead to stroke. AF is also associated with increased risks of congestive heart failure and cardiomyopathy. These risks warrant medical attention for patients with AF even if the symptoms are mild. Atrial fibrillation is the most common sustained heart rhythm disorder and increases the risk for heart disease and stroke, both leading causes of death in the United States. Over 2 million adults in the United States have been diagnosed with atrial fibrillation.

Various ablation techniques have been proposed to treat atrial fibrillation, including the Cox-Maze procedure, linear ablation of various regions of the atrium, and circumferential pulmonary vein ablation. Each of these techniques has its various drawbacks. The Cox-Maze procedure and linear ablation procedures are tedious and time-consuming, taking up to several hours to accomplish endocardially. Circumferential ablation is proving to lead to rapid stenosis and occlusion of the pulmonary veins. Thus, improved atrial ablation techniques are sorely needed.

SUMMARY OF THE INVENTION

The devices and methods described below provide for a simplified approach to the treatment of atrial fibrillation with substantially improved efficacy & outcomes in patients with paroxysmal or persistent atrial fibrillation. An endocardial catheter with an electrode array particularly adapted to locate and ablate foci of arrhythmia which are required for sustained atrial fibrillation is provided. The array is easily deployed and retracted from the catheter, and presents a distally oriented electrode array that can be pressed flat against the wall of the atrium. A control system comprising an ECG analyzer and a RF power supply operates to analyze electrical signals obtained from the electrode array, determine if an arrythmogenic focus is present in the area covered by the array, and supply RF power to appropriate electrodes to ablate the focus.

BRIEF DESCRIPTION OF THE DRAWINGS

FIG. 2 illustrates an atrial sensing and ablation catheter with an expandable electrode array constrained within an outer catheter tube.

FIG. 3 is an enlarged view of the distal portion of the catheter of FIG. 2.

FIG. 4 is a cross-section of the distal portion of the catheter of FIG. 2.

FIG. 5 illustrates the atrial sensing and ablation catheter of FIG. 2 with the electrode array in its expanded configuration.

FIG. 6 is an enlarged view of the electrode array in its expanded configuration.

FIG. 7 is an end view of the electrode array in its expanded configuration.

FIGS. 8 and 9 illustrate the mechanism of recapture of the electrode array of the atrial ablation catheter.

FIG. 10 illustrates an alternate mechanism of recapture of the electrode array of the atrial ablation catheter.

FIG. 11 illustrates the operation of the steering system of the atrial ablation catheter.

FIG. 12 illustrates the electrode array in the configuration it takes on when pressed against a surface.

FIG. 13 illustrates the electrode array in the configuration it takes on when pressed against a concave surface such as the atrial wall.

DETAILED DESCRIPTION OF THE INVENTION

Figure 1:
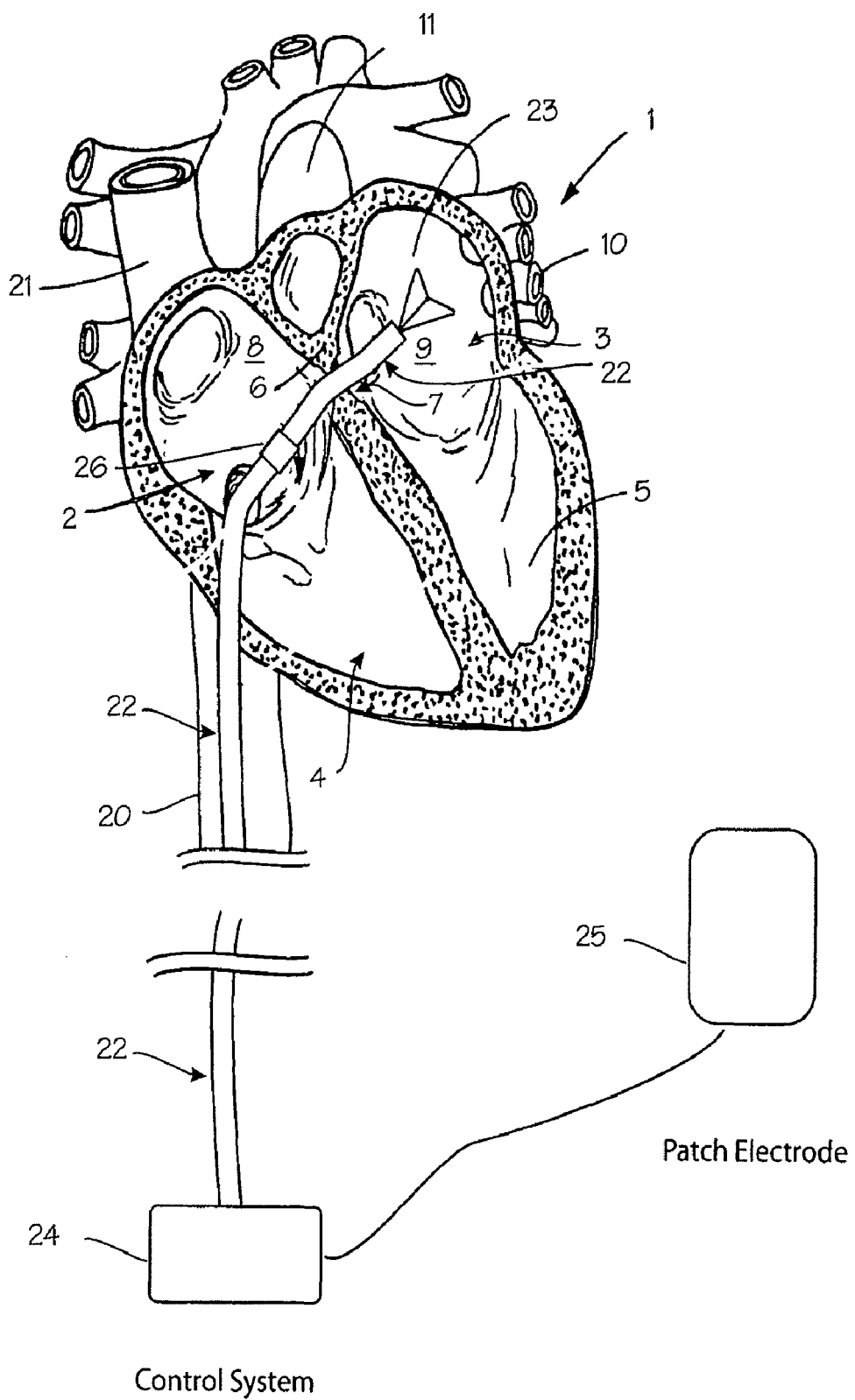
FIG. 1 illustrates the treatment to be accomplished with the devices and methods described below.

FIG. 1 illustrates the treatment to be accomplished with the devices and methods described below. FIG. 1 shows a cutaway view of the human heart 1, showing the major structures of the heart including the right atrium 2, the left atrium 3, the right ventricle 4, and the left ventricle 5. The atrial septum 6 separates the left and right atria. The fossa ovalis 7 is a small depression in the atrial septum which is easily punctured and easily heals, and may be used as an access pathway to the left atrium from the right atrium. In a patient suffering from atrial fibrillation, aberrant electrically conductive tissue may be found in the atrial walls 8 and 9, as well as in the pulmonary veins 10 and pulmonary arteries 11. Ablation of these areas, referred to as arrhythmogenic foci (and also referred to as drivers or rotors), is an effective treatment for atrial fibrillation. Though circumferential ablation of the pulmonary veins cures the arrhythmia which originates in the pulmonary veins, it often results in rapid stenosis of the pulmonary veins. Ablation of foci, rotors or drivers on atrial walls, however, may prevent the propagation of any aberrant electrical activity that originates in the pulmonary veins.

To accomplish this, a catheter is inserted into the atrium, preferably through the inferior vena cava 20, as shown in the illustration, or through the superior vena cava 21, into the right atrium or left atrium. When passing into the left atrium, as illustrated, the catheter penetrates the fossa ovalis (a transseptal puncture will facilitate the crossing). The catheter 22 carries a distal electrode array 23 into the atrium, and this electrode array is adapted to be pressed into contact with the atrial wall. The electrode array is electrically connected to circuitry in a control system 24 which is operable to analyze electrical signals detected by the electrodes and pass RF current through the electrodes and heart tissue to ablate the tissue. A surface electrode 25 is mounted on the patient's body (typically on the back) to permit use of the electrodes in monopolar modes. A return electrode 26 may also be provided on the catheter 22, proximal to the electrode array 23. Using the catheter, an electrophysiologist will map regions of the atrial walls and apply energy through the catheter to ablate any arrhythmogenic foci which are identified in the mapping procedure. The procedure may be repeated as necessary throughout the atrium.

FIG. 2 illustrates an atrial sensing and ablation catheter 22 with an expandable electrode array. The catheter comprises a handle 30 with a steering control knob 31, electrical connector 32 and side-arm connector 33. The electrical connector is used to connect the catheter to the control box. An outer catheter tube 34 is slidably mounted on the inner catheter tube 35, and they may be releasably secured to each other by sliding the proximal portion of the outer catheter sheath strain relief 36 over the cylindrical detent 37 which is fixed to the handle. The side arm connector is used as a flushing port, to allow the flushing of debris and blood from the space between the inner and outer catheter tubes. The electrode array 23 is fixed to the inner catheter tube 35, and is restrained within the distal portion of the outer catheter tube 34.

FIG. 3 is an enlarged view of the distal portion of the catheter of FIG. 2. The electrode array 23 comprises a number of resiliently biased arms 39 which each carry a number of electrodes 40. An array of five arms, each of which carry two electrodes, is suitable for use in the atria. The arms each comprise a wire (preferably a flat wire) with a distal section 41, a proximal section 42 and an intervening bend section 43. The electrodes are placed on the distal sections. The proximal end of each arm is fixed to the inner catheter tube 35. The distal end of each arm is fixed to the floating tube (or pin) 44. This floating tube is retained within the inner catheter tube, but is free to slide longitudinally within the inner catheter tube. The necessary electrical wires 45 and 46 which connect the electrodes to the control system run from each electrode proximally along the arm (and through any intervening electrodes), and enter the lumen of the floating tube 44 and then run proximally through the inner catheter tube and into the catheter handle. (Additional wires for temperature sensing thermistor or thermocouples may be included.) The wires are looped within the handle to provide the distension necessary for the resilient deployment of the electrode array as illustrated in FIG. 5. A steering pull wire 47 is secured to the distal end of the inner catheter tube. The pull wire runs proximally to the steering control knob in the proximal handle, and is operably connected to the control knob so that rotation of the control knob pulls the pull wire to effectuate steering of the distal end of the device. The outer catheter tube is sufficiently flexible so that it is steered by deflection of the inner catheter tube. The materials used for each component are selected to provide the suitable flexibility, column strength and steerability. The outer catheter tube 34 may comprises nylon, polyester or other suitable polymer, and the inner catheter tube 35 comprises a stainless steel coil covered in shrink tubing to provide tensile strength. The electrode arms 39 comprise flat nitinol wires. The floating tube 44 comprises a stainless steel coil. The floating tube may be disposed over the inner catheter if accommodations are made for proximal fixation of the proximal arm segments to the inner catheter, such as placing the fixation points proximally on the inner catheter or providing slots on the proximal portion of the floating tube. The electrode wires may be disposed on or in the wall of the inner catheter, rather than passing through the lumen of the inner catheter as shown in the Figures.

FIG. 4 is a cross-section of the distal portion of the catheter of FIG. 2. At this cross section, an electrode 40 is mounted on each arm 39. These electrodes will be located on the inner portion of the deployed array as shown in FIGS. 5 and 6. The electrodes are tubes of triangular cross section, with tissue contacting faces directed radially outwardly from the catheter. The electrode wires 45, which are connected to the outside electrodes, run through the inside electrodes on their route to the floating tube. The electrode wires 46 are fixed to the inner wall of the inner electrode. As shown in this view, the electrodes are collapsed upon the floating tube 44, and due to the triangular shape they are securely packed within the outer catheter tube 34. The floating tube 44 also houses the various electrode wires 45 and 46.

FIGS. 5 and 6 illustrate the atrial sensing and ablation catheter of FIG. 2 with the electrode array in its expanded configuration. The outer catheter tube 34 has been withdrawn proximally over the catheter inner tube, allowing the array arms 39 to expand to create substantially triangular array segments. Each proximal arm segment resiliently bends radially outwardly from the proximal connection with the inner catheter tube, while each distal arm segment bends radially inwardly from the bend portion toward the longitudinally axis of the catheter. Preferably, the distal arm segments also tend proximally, and establish an acute angle a with the proximal arm segment from which it extends, and the angle is small such that the distal end of the distal arm segment (the point of attachment to the floating tube) is proximal to the bend point. The angle b, which is the angle between the long axis of the catheter and the proximal arm segment, is also an acute angle. The angle c between the catheter longitudinal axis and the distal arm segment is thus obtuse, creating a forward biased array. Generally, the forward biased array results from providing a bend angle a which is less than 90−b, or, conversely, providing a bend angle a such that a+b is less than 90°. In embodiments where the arm segments are not straight, the overall curvature of the arms may provide an arc such that the angle b is acute and the angle c is obtuse.

The resilient expansion of the electrode array pushes the floating tube 44 proximally into the inner catheter tube. When the outer catheter tube is pushed distally over the electrode array, the distal electrode arms will be forced distally, as the proximal segments are compressed inwardly starting from the proximal end, to first splay the distal segments toward and through a perpendicular relationship with the floating tube such that the joint between the arms and the floating tube is distal to the bend point, while drawing the floating tube distally within the inner catheter tube.

FIG. 7 is an end view of the electrode array in its expanded configuration. In this view, the five arm array is fully expanded resiliently and resiliently flattened as if pressed against a flat surface, to create a substantially planar arrangement of the distal arm segments and the electrodes. The array provides two pairs of electrodes on each of five arms evenly distributed about the floating tube 44. The electrode wires 45 and 46 can be seen extending inwardly from the electrodes and running proximally down the floating tube. The arms are each separated from the adjacent arms by about 72°, for form a pentagram (the actual shape obtained within the heart will of course diverge from the ideal due to resilient deformation as the array is pressed against the atrium walls). The array, when deployed and flattened as shown, is preferably about 15 to 30 mm in diameter (to the outer extent of the arm), with each distal arm segment 41 being about 7.5 to 15 mm long. The diameter of the electrode group (from the center to the outer extent of the electrodes) is preferably about 2 to 30 mm. The wire width is preferable about 0.26 mm, and the distal face of the electrodes is preferably about 1 to 2 mm wide and 2 to 3 mm long (the illustrated electrodes are 2 mm wide and 1.6 mm wide). The electrode array can comprise any number of arms, and each arm can carry any number of electrodes, though the five arm array, with dimensions described above, is well suited for the typical atrial ablation therapy.

FIGS. 8 and 9 illustrate the mechanism of recapture of the electrode array. When the outer catheter tube 34 is pushed distally over the inner catheter tube 35 and the electrode array, the distal electrode arms 41 will be forced distally, as the proximal segments 42 are compressed inwardly starting from the proximal end, as shown in FIG. 8. This initially splays the distal segments toward a perpendicular relationship with the floating tube as shown in FIG. 8. As the outer catheter tube is translated further distally, such that the joint between the arms and the floating tube is distal to the bend point, the distal arm segments become further splayed, such that they are distal to the proximal arms segments. Because the distal arm segments are fixed to the floating tube, their movement distally draws the floating tube distally within the inner catheter tube. The array is completely captured when the outer catheter tube is translated fully forward to resume the position shown in FIGS. 2 and 3. As can be seen from the illustration, the bend sections provide a means for rotatably joining the distal arm segment to the proximal arm segment, and other suitable mechanisms, such as hinges, may be used instead.

FIG. 10 illustrates an alternate mechanism of recapture of the electrode array of the atrial ablation catheter. In the device shown in FIG. 10, the small diameter configuration is achieved by folding the distal arm segments axially inside the proximal arm segments. This is achieved by biasing the proximal arm segments to bow outwardly, providing an inward component of force when compressed by action of the outer catheter tube. Recapture of the array after use may be aided by pulling proximally on the floating tube with a control wire operable from the proximal handle.

FIG. 11 illustrates the operation of the steering system of the atrial ablation catheter. The steering pull wire 47 is secured to the distal end of the inner catheter tube 35, such that pulling the pull wire proximally deflects the distal end of the inner catheter tube. Using the pull wire, the operator can steer the array as needed to contact different areas of the atrium wall. The pull wire may, as shown, be unsecured to the inner catheter tube wall along much of its length, or it may be embedded in the inner catheter tube wall or otherwise restrained to the inner catheter tube. The entire distal end of the catheter may also be steered with this pull wire, as the outer catheter tube is sufficiently flexible that it will deform along with the inner catheter tube. If desired, similar steering can be effected with a pushable wire or stylet in place of the pull wire.

FIG. 12 illustrates the electrode array in the configuration it takes on when pressed against the atrial wall. After the array has been steered to face a target site within the atrium, the operator will press the distal face of the array into contact with the atrium wall, and this may cause the distal face to deform, resiliently, to a substantially flat configuration as shown. Given the concave curvature of the atrium chamber, the array will deform to obtain distal arm segments with slightly convex curvature as shown in FIG. 12.

Figure 14:
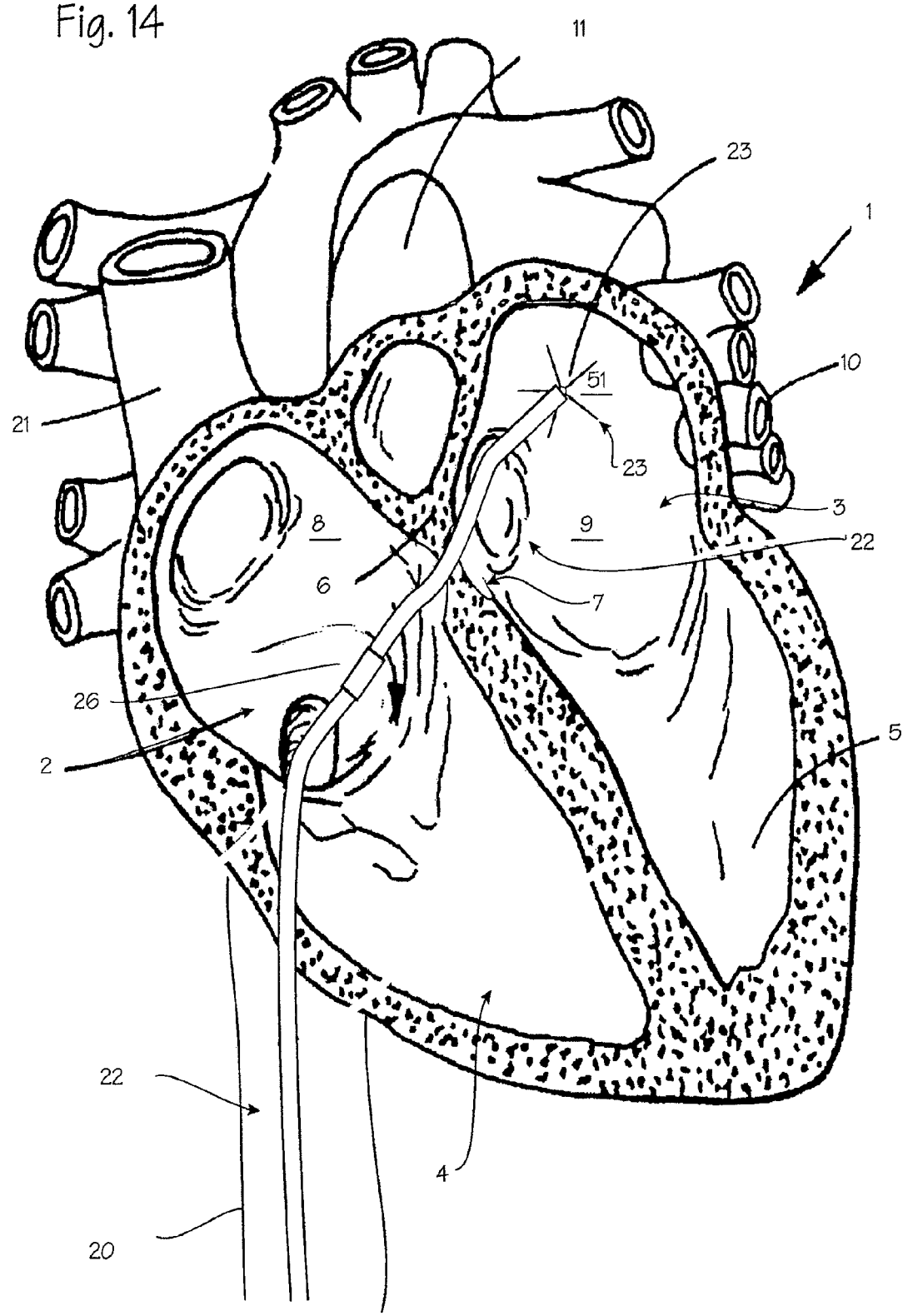
FIG. 14 illustrates a method for using the electrode array in a monopolar mode.

After contact has been established between the atrium wall and the electrode array, the operator will analyze electrical signals detected by the electrodes to determine if the array has been placed over an arrhythmogenic focus. If it has, the operator may energize any of the electrodes, as appropriate, to ablate the focus. Bipolar RF energy may be applied between pairs of the electrodes, or monopolar energy may be applied to any of the electrodes (grounded to the surface electrode or a return electrode located proximally on the catheter body). FIG. 14 illustrates a method for using the electrode array in a monopolar mode, especially in sensitive areas of the atrium such as the back wall (the posterior wall) and the ostia of the pulmonary veins. As shown, the electrode array is placed over the posterior wall 51 of the left atrium, with electrodes in contact with the atrium wall. This wall is fairly thin, and the patient's esophagus lies immediately behind this wall. Ablation in this area entails a risk of perforating the atrial wall and the esophagus. To reduce this risk, the electrode array is operated in a monopolar mode. For each arrhythmogenic focus found by the electrophysiologist (based on the electrical signals detected by the various electrodes), an appropriate electrode can be energized in a monopolar mode to direct ablative RF power to the atrial wall, while the return electrode 26 provides a ground for the RF energy. With the return electrode on the catheter, the current densities around the electrode will be sufficient to locally ablate the atrial wall, but because the RF energy takes a path toward the return electrode, the current density at the epicardial surface of the atrium, and in surrounding structures such as the esophagus, will be minimized. The device may be used is this mode to ablate the ostium of a pulmonary vein, and treatment of the ostium may include additional steps of ablating the ostium with the electrode in a first orientation, then rotating the electrode array and maintaining (or re-establishing) contact with the ostium to establish contact in a second orientation and then ablating the ostium with the electrode in the second orientation, and repeating as necessary to create a ring of ablated zones establishing substantially circumferential ablation of the pulmonary vein ostium.

Though the ablation device has been described in terms of its preferred endocardial and transcutaneous method of use, the array may be used on the heart during open heart surgery, open chest surgery, or minimally invasive thoracic surgery. Thus, during open chest surgery, a short catheter or cannula carrying the electrode array may be inserted into the heart through the wall of the right atrium or through the vena cava, or an electrode array may be applied directly to the atrium wall through an incision in the left atrium wall. Also, the electrode array may be applied to the epicardial surface of the atrium or other areas of the heart to detect and ablate arrhythmogenic foci from outside the heart.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

What is claimed is:

1. An ablation catheter adapted to ablate atrial wall tissue, comprising:
   an inner catheter tube;
   an outer catheter tube slidably mounted on the inner catheter tube;
   an electrode array having at least two resilient arms coupled to the inner catheter tube, each of the at least two resilient arms having a delivery configuration and an expanded configuration and comprising a distal arm section, a proximal arm section, and a bend section disposed between the distal arm section and the proximal arm section; and
   a plurality of electrodes coupled to the distal arm section of each of the at least two resilient arms, wherein each of the resilient arms is disposed within the outer catheter tube in the delivery configuration and each of the resilient arms is withdrawn from the outer catheter tube in the expanded configuration to form a planar array of substantially triangular faces oriented parallel to a longitudinal axis of the catheter.

2. The ablation catheter of claim 1, wherein the at least two resilient arms are adapted to bend at the bend section when it expands from the delivery configuration to the expanded configuration.

3. The ablation catheter of claim 1 wherein the proximal arm section forms an acute angle with the distal arm section at the bend section when the at least two resilient arm are in the expanded configuration.

4. The ablation catheter of claim 1 wherein the at least two resilient arms comprises a wire.

5. The ablation catheter of claim 1 further comprising a pin extending into the inner catheter tube, the pin being longitudinally slidable relative to the inner catheter tube.

6. The ablation catheter of claim 5 wherein the proximal arm section is attached to the inner catheter tube and the distal arm section is attached to the pin.

7. The ablation catheter of claim 1 further adapted to map atrial wall tissue.

8. The ablation catheter of claim 1 wherein the bend section is pre-formed in the at least two resilient arms.

9. An ablation catheter adapted to ablate atrial wall tissue, comprising:
an inner catheter tube;
an outer catheter tube slidably mounted on the inner catheter tube;
an electrode array having at least two resilient arms coupled to the inner catheter tube, each of the at least two resilient arms having a delivery configuration and an expanded configuration and comprising a distal arm section, a proximal arm section, and a bend section disposed between the distal arm section and the proximal arm section; and
a plurality of electrodes coupled to the distal arm section of the at least two resilient arms, wherein each of the resilient arms is disposed within the outer catheter tube in the delivery configuration and each of the resilient arms self-expands in the expanded configuration responsive to withdrawal of the outer catheter tube to form a planar array of triangular faces.

10. The ablation catheter of claim 9, wherein the at least two resilient arms are adapted to bend at the bend section when it expands from the delivery configuration to the expanded configuration.

11. The ablation catheter of claim 9 wherein the proximal arm section forms an acute angle with the distal arm section at the bend section when the at least two resilient arms are in the expanded configuration.

12. The ablation catheter of claim 9 wherein the at least two resilient arms comprises a wire.

13. The ablation catheter of claim 9 further comprising a pin extending into the inner catheter tube, the pin being longitudinally slidable relative to the inner catheter tube.

14. The ablation catheter of claim 13 wherein the proximal arm section is attached to the inner catheter tube and the distal arm section is attached to the pin.

15. The ablation catheter of claim 9 further adapted to map atrial wall tissue.

16. The ablation catheter of claim 9 wherein the bend section is preformed in the at least two resilient arms.

17. An ablation catheter adapted to ablate atrial wall tissue, comprising:
an inner catheter tube;
an outer catheter tube slidably mounted on the inner catheter tube;
an electrode array having at least two resilient arms coupled to the inner catheter tube, each of the at least two resilient arms having a delivery configuration and an expanded configuration and comprising a distal arm section, a proximal arm section, and a bend section disposed between the distal arm section and the proximal arm section; and
a plurality of electrodes coupled to the distal arm section of each of the at least two resilient arms, wherein each of the resilient arms is disposed within the outer catheter tube in the delivery configuration and each of the resilient arms is withdrawn from the outer catheter tube in the expanded configuration;
in the expanded configuration, the distal arm sections extend radially outward from the inner catheter tube and resiliently form a plane substantially perpendicular to a longitudinal axis of the catheter.

* * * * *

UNITED STATES PATENT AND TRADEMARK OFFICE
CERTIFICATE OF CORRECTION

| | | |
|---|---|---|
| PATENT NO. | : 8,273,084 B2 | Page 1 of 1 |
| APPLICATION NO. | : 12/197425 | |
| DATED | : September 25, 2012 | |
| INVENTOR(S) | : Christopher G. Kunis et al. | |

It is certified that error appears in the above-identified patent and that said Letters Patent is hereby corrected as shown below:

On page 4, the ninth EP reference listed under FOREIGN PATENT DOCUMENTS is:

EP     13844456  B1  2/2006

It should be corrected as follows:

EP     1384445  B1  2/2006

Signed and Sealed this
Fourth Day of December, 2012

David J. Kappos
*Director of the United States Patent and Trademark Office*